US011085902B2

(12) United States Patent
Athanassiadis

(10) Patent No.: US 11,085,902 B2
(45) Date of Patent: Aug. 10, 2021

(54) OPTICAL BREAKDOWN ACOUSTIC TRANSDUCER

(71) Applicant: Massachusetts Institute of Technology, Cambridge, MA (US)

(72) Inventor: Athanasios G. Athanassiadis, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 157 days.

(21) Appl. No.: 16/116,561

(22) Filed: Aug. 29, 2018

(65) Prior Publication Data

US 2019/0094185 A1 Mar. 28, 2019

Related U.S. Application Data

(60) Provisional application No. 62/551,548, filed on Aug. 29, 2017.

(51) Int. Cl.
*G01N 29/24* (2006.01)
*G01N 29/032* (2006.01)
(Continued)

(52) U.S. Cl.
CPC ........... *G01N 29/2418* (2013.01); *A61B 8/12* (2013.01); *A61B 17/225* (2013.01); *G01N 29/032* (2013.01); *G01N 29/06* (2013.01)

(58) Field of Classification Search
CPC .. G01N 29/2418; G01N 29/032; G01N 29/06; A61B 8/12; A61B 17/225
(Continued)

(56) References Cited

U.S. PATENT DOCUMENTS

| 4,608,979 A * | 9/1986 | Breidenthal | A61B 17/225 601/4 |
| 5,224,942 A * | 7/1993 | Beuchat | A61B 18/26 606/128 |

(Continued)

OTHER PUBLICATIONS

International Search Report and Written Opinion in International Patent Application No. PCT/US2018/048582 dated Nov. 26, 2018, 15 pages.
(Continued)

*Primary Examiner* — Peter J Macchiarolo
*Assistant Examiner* — Monica S Young
(74) *Attorney, Agent, or Firm* — Smith Baluch LLP

(57) ABSTRACT

An optical breakdown acoustic transducer can generate high-bandwidth, high amplitude acoustic waves via an optical breakdown process. The optical breakdown acoustic transducer can include a vessel having an interior cavity that is substantially filled with a fluid and a light source that emits light. The light can be directed through an optical element that focuses the light to at least one focal point located within the fluid, thereby causing optical breakdown and generation of an acoustic shockwave. The acoustic shockwave can then be coupled into a medium surrounding the optical breakdown acoustic transducer via an acoustic outlet coupled to the vessel. The acoustic output of the optical breakdown acoustic transducer can be tuned by adjusting the properties of the optical source and/or the shape of the cavity containing the fluid. The optical breakdown acoustic transducer can be used for imaging, sensing, communication, and mechanical disruption.

21 Claims, 11 Drawing Sheets

(51) Int. Cl.
    *G01N 29/06* (2006.01)
    *A61B 8/12* (2006.01)
    *A61B 17/225* (2006.01)
(58) Field of Classification Search
    USPC .......................................................... 73/643
    See application file for complete search history.

(56) References Cited

U.S. PATENT DOCUMENTS

| | | | | |
|---|---|---|---|---|
| 7,613,074 | B1* | 11/2009 | Blackmon | H04B 11/00 367/134 |
| 8,394,084 | B2* | 3/2013 | Palankar | A61B 90/361 606/6 |
| 2001/0003800 | A1* | 6/2001 | Crowley | A61B 5/0059 607/88 |
| 2004/0102821 | A1* | 5/2004 | Kawata | A61B 8/06 607/89 |
| 2005/0251116 | A1* | 11/2005 | Steinke | A61B 18/20 |
| 2008/0114419 | A1* | 5/2008 | Crowley | A61B 6/4057 607/92 |
| 2008/0189932 | A1* | 8/2008 | Sliwa | G10K 11/30 29/594 |
| 2009/0069794 | A1* | 3/2009 | Kurtz | A61F 9/00825 606/4 |
| 2010/0087735 | A1* | 4/2010 | Hall | G10K 11/30 600/437 |
| 2011/0230826 | A1* | 9/2011 | Yoh | A61M 5/30 604/70 |
| 2015/0005613 | A1* | 1/2015 | Kim | G01N 29/0654 600/407 |
| 2015/0133848 | A1* | 5/2015 | Bratchenia | A61B 18/203 604/20 |
| 2015/0351724 | A1 | 12/2015 | Guo et al. | |
| 2016/0271419 | A1* | 9/2016 | Varghese | A61B 18/203 |
| 2016/0278629 | A1* | 9/2016 | Schuele | A61B 3/117 |
| 2017/0254889 | A1* | 9/2017 | Papanicolau | A61B 8/483 |
| 2019/0099612 | A1* | 4/2019 | Hiereth | A61B 5/0084 |

OTHER PUBLICATIONS

Karpiouk et al. "Ultrasound characterization of cavitation microbubbles produced by femtosecond laser pulses." Optical Interactions with Tissue and Cells XX. vol. 7175. International Society for Optics and Photonics, 2009. 7 pages.

Niemi et al., "Investigation of the photoacoustic signal dependence on laser power." Advanced Laser Technologies 2007. vol. 7022. International Society for Optics and Photonics, 2008. 9 pages.

Antonelli et al., Experimental demonstration of remote, passive acousto-optic sensing. The Journal of the Acoustical Society of America. Dec. 2004;116(6):3393-403.

Blackmon et al., Experimental demonstration of multiple pulse nonlinear optoacoustic signal generation and control. Applied optics. Jan. 1, 2005;44(1):103-12.

Blackmon et al., Linear optoacoustic underwater communication. Applied optics. Jun. 20, 2005;44(18):3833-45.

Brelet et al., Underwater acoustic signals induced by intense ultrashort laser pulse. The Journal of the Acoustical Society of America. Apr. 2015;137(4):EL288-92.

Fortes et al., A study of underwater stand-off laser-induced breakdown spectroscopy for chemical analysis of objects in the deep ocean. Journal of Analytical Atomic Spectrometry. 2015;30(5):1050-6.

Georgiev et al., Generation of flexural waves in plates by laser-initiated airborne shock waves. Journal of Sound and Vibration. Jan. 17, 2011;330(2):217-28.

Han et al., Dynamics of laser-induced bubble pairs. Journal of Fluid Mechanics, 771:706-742, Apr. 2015.

Hornstein et al., Optical bandwidth and focusing dynamics effects on an underwater laser acoustic source. In Lasers and Electro-Optics, 2009 and 2009 Conference on Quantum electronics and Laser Science Conference. CLEO/QELS 2009. Conference on 2009 Jun. 2 (pp. 1-2). IEEE.

Hosoya et al., Acoustic testing in a very small space based on a point sound source generated by laser-induced breakdown: Stabilization of plasma formation. Journal of Sound and Vibration. Sep. 16, 2013;332(19):4572-83.

Hutchins, Ultrasonic generation by pulsed lasers. In Physical Acoustics Jan. 1, 1988 (vol. 18, pp. 21-123). Academic press.

Jones et al., Remote underwater ultrashort pulse laser acoustic source. InLasers and Electro-Optics, 2006 and 2006 Quantum Electronics and Laser Science Conference. CLEO/QELS 2006. Conference on May 21, 2006 (pp. 1-2). IEEE.

Lauterborn et al., Experimental investigations of cavitation-bubble collapse in the neighbourhood of a solid boundary. Journal of Fluid Mechanics. Nov. 1975;72(2):391-9.

Lauterborn et al., Shock Wave Emission by Laser Generated Bubbles. In Can F Delale, editor, Bubble Dynamics and Shock Waves, pp. 1-37. Springer Berlin Heidelberg, Berlin, Heidelberg, 2013.

Lazic et al., Insights in the laser-induced breakdown spectroscopy signal generation underwater using dual pulse excitation—Part I: Vapor bubble, shockwaves and plasma. Spectrochimica Acta Part B: Atomic Spectroscopy. Apr. 1, 2013;82:42-9.

Lyon et al., Multi-point laser spark generation for internal combustion engines using a spatial light modulator. Journal of Physics D: Applied Physics. Nov. 5, 2014;47(47):475501.

Noack et al., Influence of pulse duration on mechanical effects after laser-induced breakdown in water. Journal of Applied Physics. Jun. 15, 1998;83(12):7488-95.

Noack et al., Laser-induced plasma formation in water at nanosecond to femtosecond time scales: calculation of thresholds, absorption coefficients, and energy density. IEEE journal of quantum electronics. Aug. 1999;35(8):1156-67.

Schaffer et al., Thresholds for femtosecond laser-induced breakdown in bulk transparent solids and water. In Andreas K Freund, Henry P Freund, and Malcolm R Howells, editors, SPIE's International Symposium on Optical Science, Engineering, and Instrumentation, pp. 2-8. SPIE, Dec. 1998.

Shen, The principles of nonlinear optics. New York, Wiley-Interscience, 1984, 575 p. 1984. 13 pages.

Stelmaszczyk et al., Long-distance remote laser-induced breakdown spectroscopy using filamentation in air. Applied Physics Letters. Nov. 1, 2004;85(18):3977-9.

Toytman et al., Optical breakdown in transparent media with adjustable axial length and location. Optics Express, (24):24688-24698, Nov. 18, 2010.

Vogel et al., Acoustic transient generation by laser?produced cavitation bubbles near solid boundaries. The Journal of the Acoustical Society of America. Aug. 1988;84(2):719-31.

Vogel et al., Energy balance of optical breakdown in water at nanosecond to femtosecond time scales. Applied Physics B. Feb. 1, 1999;68(2):271-80.

Vogel et al., Plasma formation in water by picosecond and nanosecond Nd:YAG laser pulses. I. Optical breakdown at threshold and superthreshold irradiance. IEEE Journal of Selected Topics in Quantum Electronics, 2(4):847-860, Dec. 1996.

Vogel et al., Shock wave emission and cavitation bubble generation by picosecond and nanosecond optical breakdown in water. The Journal of the Acoustical Society of America. Jul. 1996;100(1):148-65.

Ye et al., Underwater material recognition based on laser-induced acoustic source. InOceans 2014—Taipei Apr. 7, 2014 (pp. 1-4). IEEE.

* cited by examiner

OPTICAL BREAKDOWN ACOUSTIC TRANSDUCER

CROSS-REFERENCE TO RELATED PATENT APPLICATION(S)

This application claims priority, under 35 U.S.C. § 119(e), to U.S. Application No. 62/551,548, which was filed on Aug. 29, 2017, and is incorporated herein by reference in its entirety.

GOVERNMENT SUPPORT

This invention was made with Government support under Contract No. FA8721-05-C-0002 awarded by the United States Air Force and Contract No. N00014-18-1-2066 awarded by the Office of Naval Research. The Government has certain rights in the invention.

BACKGROUND

Optical breakdown is a physical phenomenon discovered in 1962. It can be used to excite a plasma in a target material. During optical breakdown (also referred to as "laser-induced breakdown" or "dielectric breakdown"), a high-power pulsed laser is focused tightly to a small focal volume, where nonlinear interactions with the ambient medium ionize a plasma and cause the incident light to be efficiently absorbed. Plasma formation can take place in solids, liquids, and gasses. For all media, the laser light is focused so that the beam irradiance (power flux per unit area) surpasses a critical 'irradiance threshold,' which is itself a function of target material, pulse duration, and wavelength. For example, the irradiance threshold for water is about $10^{10}$ W/cm$^2$. The signatures of optical breakdown are optical emission and an acoustic shock wave produced by the plasma. In a solid breakdown can be accompanied by material removal (ablation), and in a liquid is accompanied by the growth of a gas bubble (cavitation).

The properties of the acoustic shock have been studied extensively in the academic literature, and the shock's dependence on system properties have been described. The acoustic shock wave produced by optical breakdown slows to a linear acoustic wave that can exceed peak pressures levels of 200 dB re 1 µPa at 1 m. The shockwave duration is set, in part, by the laser pulse duration, so short (e.g., nanosecond) optical pulses produce ultra-high bandwidth acoustic sources.

Current applications of optical breakdown include free-space communications, material processing, material identification, nondestructive testing, ophthalmic surgery, and spark ignition in engines.

SUMMARY

Embodiments described herein are directed to an optical breakdown acoustic transducer for generating acoustic shockwaves via optical breakdown. The optical breakdown acoustic transducer includes a vessel having an interior cavity that is substantially filled with a fluid and a light source that emits light. The light is directed through an optical element optically coupled to the vessel, which focuses the light to at least one focal point located within the fluid, thereby causing optical breakdown and generation of an acoustic shockwave. The acoustic shockwave is then coupled into a medium surrounding the optical breakdown acoustic transducer via an acoustic outlet coupled to the vessel.

An exemplary realization of an optical breakdown acoustic transducer can be used to generate a collimated acoustic beam. The optical breakdown acoustic transducer can include a light source located separately from a vessel that emits an optical beam, which is delivered to the vessel via an optical fiber. The vessel can have two cavities, the first cavity containing optical elements to shape the optical beam and the second cavity containing a fluid. The optical beam can be focused to a breakdown site (e.g., a focal point of the optical element(s)), from which a spherical acoustic shockwave is generated and propagates within the fluid in the second cavity. The acoustic wave is then collimated by an acoustic lens, and then propagates out for communication or sensing as a collimated beam.

Another exemplary optical breakdown acoustic transducer can form three breakdown sites, producing an acoustic beam with a complex wave front. The optical breakdown acoustic transducer can include a vessel having two cavities. The first cavity can contain a light source (e.g., a diode laser) that emits a pulsed optical beam and optical elements to shape the pulsed optical beam. A spatial light modulator (SLM) can be included as one of the optical elements. The SLM can actively adjust the spatial wave front of the optical beam such that three (pulsed) optical beams having three focal points are formed. The second cavity can contain a fluid. The three focused optical beams can be focused at three breakdown sites in the fluid, producing three acoustic shockwaves. The acoustic waves can then be superimposed onto one another and transmit through an acoustic lens, producing an acoustic beam with a desired wave front.

Yet another exemplary optical breakdown acoustic transducer may be disposed on a tip of a miniaturized device such as an endoscope. An optical fiber may be used to couple a light source to a vessel. The optical beam generated by the light can be directed to a condenser lens, which focuses the optical beam to a breakdown site located within a sealed cavity of the vessel containing a fluid. The condenser lens also functions as an optical window. The focused optical beam causes breakdown of the fluid at the breakdown site, thus generating an acoustic shockwave that propagates as a spherical wave towards the walls of the vessel. The portion of the walls of the vessel surrounding the cavity may be substantially spherical and can also function as an acoustic outlet. Thus, the acoustic shockwave can couple into the surrounding media as a substantially spherical wave. In this manner, the optical breakdown acoustic transducer can be used to produce a spherical acoustic point source for subsequent imaging and/or sensing.

In some instances, an optical breakdown acoustic transducer can be used to generate reconfigurable, independently timed acoustic sources having high-bandwidth and high amplitude. The acoustic output (e.g., amplitude, frequency response, wave front) of the optical breakdown acoustic transducer can be tuned by adjusting the properties of the pulses emitted by the optical source and/or the shape of the cavity containing the fluid (e.g., a sphere, a cylinder, or another geometry). The amplitude and the frequency content of the acoustic shockwave can be tuned by adjusting the power and/or the spot size of the optical pulse. The wave front of the acoustic shockwave can be tuned by the shape of the optical beam spot size, optically adjusting the position of the breakdown site within the cavity, and/or utilizing multiple breakdown sites. In particular, the position of the breakdown site can be adjusted by beam-shaping optics, which can allow for multiple operating modes where the acoustic output can be collimated, focused, or diverging. Adjustments to the optical source can be made actively on-the-fly or incorporated into the design using a particular assembly of optical elements. A small pressure sensor can also be disposed within the cavity to detect a portion of the acoustic shockwaves generated by breakdown for subsequent feedback control and/or signal analysis.

In some instances, an optical breakdown acoustic transducer can include a vessel defining a sealed cavity where a fluid may be disposed in the sealed cavity. An optical element may be in optical communication with the fluid such that the optical element has at least one focal point located within the sealed cavity. A pulsed light source that emits an optical pulse may be in optical communication with the fluid via the optical element such that the optical pulse causes breakdown of the fluid at the at least one focal point. The breakdown of the fluid results in the generation of an acoustic shockwave emanating from the at least one focal point. The vessel may also include an acoustic outlet to transmit the acoustic shockwave into at least a portion of a medium in contact with the optical breakdown acoustic transducer. The acoustic outlet may be configured to collimate the acoustic shockwave. The sealed cavity can have dimensions ranging between about 500 μm and about 1000 mm. The fluid may also substantially fill the sealed cavity. The optical pulse emitted by the pulsed light source may have a pulse duration that ranges between about 1 picoseconds to about 1 millisecond. The optical breakdown acoustic transducer may include a spatial light modulator (SLM) in optical communication with the pulse light source to modify the shape of the pulsed light source such that the at least one focal point moves from the first position to a second position within the sealed cavity. The optical breakdown acoustic transducer may include an acoustic modulator, in acoustic communication with the sealed cavity, to tune at least one of a frequency content, directionality, or amplitude of the acoustic shockwave. The optical breakdown acoustic transducer may include an acoustic receiver, in acoustic communication with the sealed cavity, to detect at least a portion of the acoustic shockwave. The optical breakdown acoustic transducer may include at least one acoustic transducer, to modify a pressure distribution within the sealed cavity so as to modify at least one of an irradiance threshold of the fluid or an optical-acoustic conversion efficiency of the breakdown.

In some instances, an optical breakdown acoustic transducer can include a pulsed light source to emit a pulsed laser beam and a beam shaping element, in optical communication with the pulsed light source, to shape a spatial wave front of the pulsed laser beam, a vessel defining a sealed cavity, and a fluid disposed in the sealed cavity. An optical element may be in optical communication with the beam-shaping element and the fluid to focus the pulsed laser beam within the fluid to at least one focal point such that the pulsed laser beam generates at least one acoustic shockwave by causing breakdown of the fluid at the at least one focal point. The optical breakdown acoustic transducer may also include an acoustic outlet on at least one side of the vessel to transmit the at least one acoustic shockwave into at least a portion of a medium surrounding the optical breakdown acoustic transducer. The beam shaping element may be a spatial light modulator. The at least one focal point may be comprised of a plurality of focal points and the at least one acoustic shockwave may be comprised of acoustic shockwaves emanating from the plurality of focal points. The pulsed laser beam may have a peak power that ranges between about 1 megawatt to about 1 gigawatt.

In some instances, a method of generating acoustic shockwaves may include the following steps: focusing at least one optical pulse to at least one position in a fluid disposed in a sealed cavity, thereby generating an acoustic shockwave emanating from the at least one position due to breakdown of the fluid and transmitting the acoustic shockwave to a portion of a medium in acoustic communication with the sealed cavity. The method of generating acoustic shockwaves may further include: measuring a characteristic of the acoustic shockwave and focusing another optical pulse within the fluid so as to generate another acoustic shockwave based on the characteristic of the acoustic shockwave. The characteristic measured may be at least one of an amplitude, waveform, or spatial radiation pattern of the acoustic shockwave. The method of generating acoustic shockwaves may also include: measuring an optical property of the breakdown of the fluid. In some cases, prior to breakdown of the fluid, the at least one position in the fluid may be seeded to improve the effectiveness of generating the acoustic shockwave. In some cases, the portion of the medium may include a sample. In such cases, the method of generating acoustic shockwaves may also include: measuring a signal emitted by the sample in response to the acoustic shockwave and transforming the signal from a time domain representation to a frequency domain representation. This may be further followed by constructing an image of the sample from the signal.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
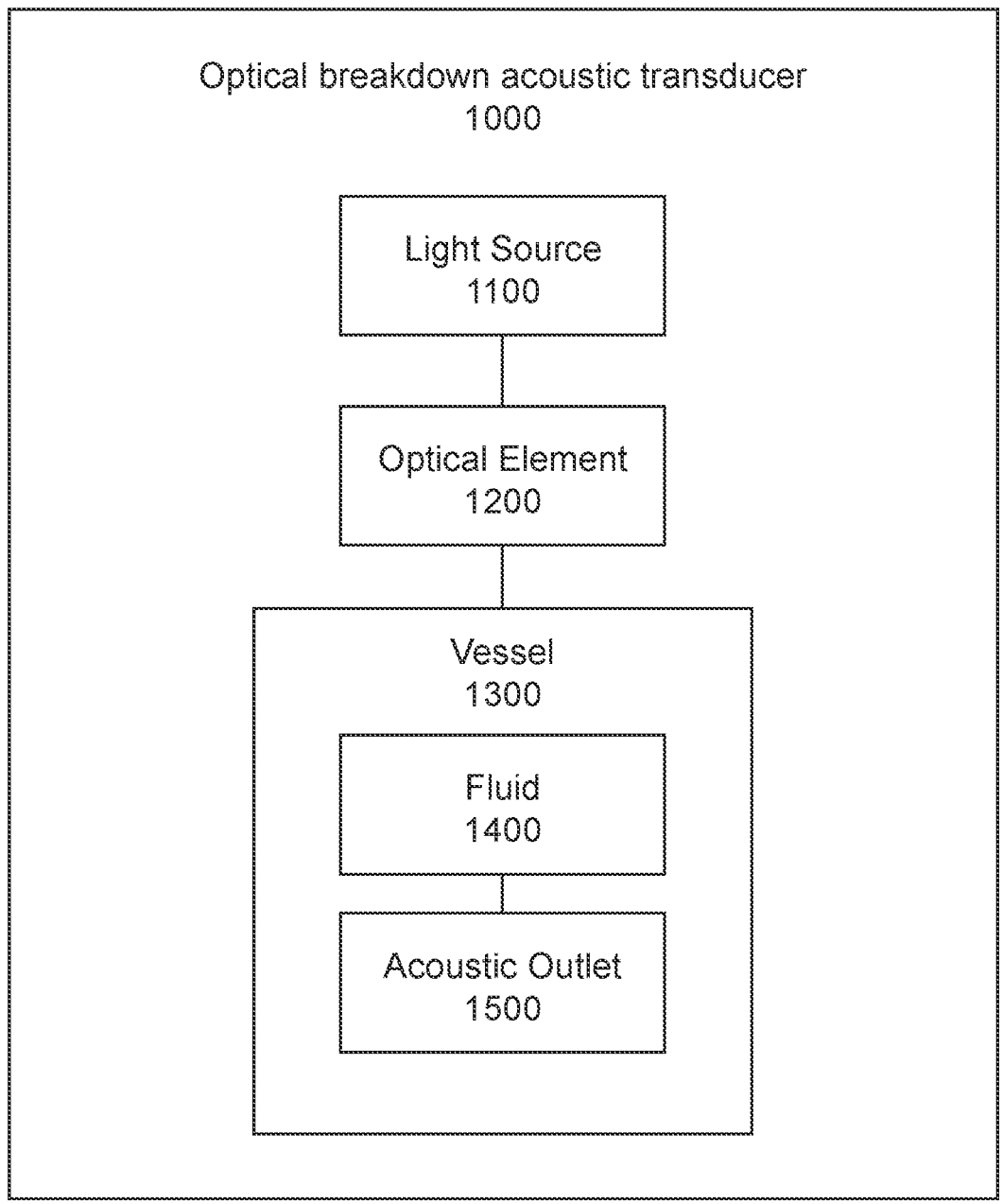
FIG. 1 is a block diagram of an exemplary optical breakdown acoustic transducer.

The present disclosure is directed to an optical breakdown acoustic transducer that includes a vessel with an enclosed interior cavity filled with a fluid. The cavity may be substantially sealed to provide greater control over the breakdown environment and to protect users from optical radiation. A pulsed light source optically coupled to the vessel can emit one or more optical pulses that can be directed to one or more optical elements having at least one focal point located within the fluid-filled cavity. For an optical pulse having an irradiance exceeding the irradiance threshold of the fluid, breakdown of the fluid can occur at the focal point (also referred to as "breakdown site") resulting in the generation of an acoustic shockwave (also referred to as an "acoustic wave"). Thus, the optically induced fluid breakdown at the focal point provides an "optical breakdown source" or "acoustic source" of acoustic shockwaves. The acoustic shockwave can then be coupled out of the cavity and into a medium at least partially surrounding the optical breakdown acoustic transducer via an acoustic outlet. In this manner, the optical breakdown acoustic transducer can produce high-intensity, high-bandwidth acoustic beams, which can be used in various applications including, but not limited to communication, sensing, imaging, and mechanical power delivery.

Compared to conventional optical breakdown sources, the enclosed transducer geometry disclosed herein produces a consistent acoustic source that is insensitive to the external environment. Compared to free-space breakdown sources, the shorter optical path of the optical breakdown acoustic transducer reduces or eliminates concerns about scatter and filamentation that can adversely affect breakdown source performance. For instance, one of the challenges of inducing optical breakdown in a free space environment (e.g., the ocean) is the scattering of light by ocean water before the plasma that breaks down the fluid can be created. Another challenge is the creation of multiple plasma 'filaments' due to a laser beam that is focused at long distances an at high powers, which may not be desirable for certain sensing tasks. In the optical breakdown acoustic transducer disclosed herein, the fluid media is enclosed within a vessel providing greater control over the breakdown process and suppressing or eliminating the challenges described above.

Additionally, the optical breakdown acoustic transducer disclosed herein can provide an ultra-high bandwidth acoustic source at high source levels. Unlike conventional ultrasonic acoustic sources, optical breakdown can produce ultra-broadband acoustic signals that span multiple orders of magnitude (decades/octaves) in frequency space using a single source. For instance, the optical breakdown acoustic transducer can emit acoustic waves at frequencies ranging between about 1 kHz to about 100 MHz with peak pressure levels of about 200 dB re 1 µPa/1 m or more in water.

Furthermore, a conventional acoustic source typically generates acoustic waves by mechanically driving a mass disposed within the device. The acoustic waves generated by the conventional source are often limited to a narrow range of frequencies. This is due, in part, to the conventional source having a narrowband acoustic resonance where acoustic waves can be generated efficiently, which arises from the presence of the driver mass. In the case of optical breakdown, sound can be generated without the use of a massive driver, which eliminates acoustic resonances from the device that would otherwise be caused by the massive driver. By generating acoustic waves in this manner, acoustic waves of any pitch over a wide range of frequencies can be readily produced. As a result, the frequency spectrum of the acoustic output from a massless system such as the optical breakdown acoustic transducer disclosed herein is substantially equal across all frequencies (e.g., the frequency response is 'flatter' across a wider frequency band).

The properties of the acoustic output (e.g., amplitude, frequency response, wave front) can also be highly tunable by adjusting the properties of the optical source and/or the cavity containing the fluid. For instance, the amplitude and the frequency content of the acoustic shockwave can be tuned by changing the power and/or the spot size of the optical pulse. The wave front of the acoustic shockwave can be tuned by the shape of the optical beam spot size, optically adjusting the position of the breakdown site within the cavity (e.g., focusing the pulse to a different point in the cavity), and/or utilizing multiple breakdown sites. In particular, the position of the breakdown site relative to an acoustic lens can be adjusted by beam-shaping optics, which can allow for multiple operating modes where the acoustic output can be collimated, focused, or diverging. For example, the breakdown site may be within the fluid, on the surface of the cavity wall, or on a thin membrane that is placed within the cavity. However, if the breakdown site is sufficiently near the cavity wall or thin membrane, ablation of the cavity wall or thin membrane may occur over time.

Adjustments to the optical source can be made actively on-the-fly or incorporated into the design using a particular assembly of optical elements. For example, a motorized optical attenuator can be used to change the power of the optical pulse or a spatial light modulator (SLM) can be used to adjust the spot size and/or the wave front of the optical beam. The cavity may also be designed with various geometries (e.g., a sphere, a cylinder, or another geometry) to modify the generation and propagation of acoustic shockwaves. The acoustic source is also omni-directional hence a small pressure sensor can be disposed within the cavity to detect the acoustic shockwaves generated by breakdown for subsequent feedback control and/or signal analysis.

Applications of Optical Breakdown Acoustic Transducers

The optical breakdown acoustic transducer described herein can benefit various applications that utilize a high-bandwidth, high-amplitude acoustic pulse. The optical breakdown acoustic transducer can expand the utility of the optical breakdown phenomenon to applications that include, but are not limited to imaging, communication, and sensing tasks in underwater acoustic communications, underwater SONAR imaging, non-destructive testing, infrastructure inspection, material characterization, and medical imaging.

In one application, the optical breakdown acoustic transducer can be used for underwater inspection and imaging operations for remote measurement of internal infrastructure properties, such as pipelines or ship hulls. By comparison, conventional systems either cannot measure internal properties of a structure or require close operating range (e.g., mm-scale or contact) to perform the operation. In an ocean environment, this can require time consuming and expensive cleaning before inspection of infrastructure.

In another application, the optical breakdown acoustic transducer may be disposed at the tip of an endoscope. By localizing a broadband acoustic source at the end of an endoscope, the endoscope can provide a substantially well-defined acoustic point source, which can be readily located by external ultrasonic imagers disposed around a patient's body. Furthermore, the external ultrasonic imagers may be scanned around a patient's body to measure the acoustic response relative to the acoustic point source, which remains in a known location within the patient's body. The external ultrasonic imagers can collect one-way acoustic transmission information (e.g., attenuation of the acoustic point source, arrival time of the acoustic wave), which can be used for clinical imaging and diagnostics.

In another application, the optical breakdown acoustic transducer can be used for lithotripsy, where the acoustic output of the optical breakdown acoustic transducer can be shaped and/or focused to produce high-pressure acoustic shocks to break apart biological materials. For example, the acoustic shocks can be used to break apart kidney stones in a patient in a non-invasive manner. Unlike conventional approaches to lithotripsy, the acoustic shock can be tuned and reconfigured using the internal optics of the optical breakdown acoustic transducer rather than the conventional method of adjust the physical motion of the lithotripter itself.

The optical breakdown acoustic transducer may also replace a downhole sparker source for oil well inspection and seismology. The vessel may be deployed down the borehole where the light source can be separately located and coupled to the vessel via an optical fiber or can be a small laser (e.g., a laser diode) contained and/or coupled to the vessel. The optical breakdown acoustic transducer can generate high-bandwidth, high amplitude acoustic waves for analysis and imaging of the oil well.

An Example Optical Breakdown Acoustic Transducer

An exemplary representation of an optical breakdown acoustic transducer 1000 is shown in FIG. 1. The optical breakdown acoustic transducer 1000 can include a vessel 1300 with an interior cavity that may be substantially filled with a fluid 1400. The optical breakdown acoustic transducer 1000 can also include a light source 1100 that emits light. The light source 1100 can direct light through an optical element 1200 optically coupled to the vessel 1300, which focuses the light to at least one focal point located within the fluid 1400, thereby causing optical breakdown and generation of an acoustic shockwave. The acoustic shockwave can then be coupled into a medium surrounding the optical breakdown acoustic transducer 1000 via an acoustic outlet 1500 coupled to the vessel 1300.

The interior cavity containing the fluid 1400 provides control of the breakdown of the fluid 1400 during operation. The interior cavity can be any suitable shape including, but not limited to a sphere, a cylinder, or a hemisphere. The vessel 1300 and the cavity may have substantially different shapes and/or dimensions, which can occur if the walls of the vessel 1300 have variable thicknesses and/or the vessel 1300 has other cavities. For example, the vessel 1300 may be substantially cylindrical in shape and define two interior cylindrical cavities where one cavity is filled with the fluid 1400 for optical breakdown.

The shape and dimensions of the cavity may be tuned to satisfy desired acoustic properties, such as increasing or decreasing reverberations and/or reflections at one or more acoustic frequencies. For example, the cavity may support one or more acoustic resonant modes (e.g., an acoustic standing wave within the cavity), which may be used to amplify the amplitude of specific acoustic frequency components generated via breakdown. In another example, the cavity may be shaped to suppress reverberations and/or reflections of acoustic waves, which can improve the quality factor of the acoustic shockwave and/or reduce the generation of air bubbles within the cavity, thus reducing optical and acoustic losses.

The dimensions of the cavity may have a lower bound defined by the spatial extent of the breakdown event itself and the optics used in the optical breakdown acoustic transducer 1000. For example, the lower bound on the dimensions of the cavity may range between about 500 μm to about 1 mm, which is suitable for generating acoustic excitation in a miniaturized device, such as an endoscope or catheter. The dimensions of the cavity may also have an upper bound defined by the decay of the pressure field. For example, a handheld device having the optical breakdown acoustic transducer 1000 with a cylindrical cavity incorporated therein, may have an upper bound on of about 76.2 mm (3 inches) for the diameter and about 101.6 mm (4 inches) for the height. In another example, the cavity may be sufficiently large (e.g., the upper bound can be about 1000 mm) to filter the acoustic output to frequencies corresponding to the cavity size.

The vessel 1300 may be designed to withstand transient shock pressures of about 1 MPa or greater. The vessel 1300 may also be designed to withstand hydrostatic pressures up to about 350 atm. For example, the optical breakdown acoustic transducer 1000 may be used in deep water environments (e.g., the bottom of an ocean or sea) for SONAR and/or acoustic imaging applications. The thickness of the walls of the vessel 1300 may also be dimensioned to meet sound isolation specifications and external pressure specifications. For instance, in deep-sea applications, the vessel 1300 should not crush, unseal, or buckle under an external pressure of about 10 atm. In another example, the optical breakdown acoustic transducer 1000 may be used in an endoscope where the thickness of the walls may be less than about 0.8 mm (1/32 inches). In yet another example, the optical breakdown acoustic transducer 1000 may be used in a handheld device where the thickness of the walls may be about 3.175 mm (1/8 inches). For a deep-water environment, the vessel 1300 may have much thicker walls to withstand higher external pressures.

The vessel 1300 can be formed from various metals, plastics, composites, ceramics, or any other suitable material or combination of materials thereof. The vessel 1300 may also be substantially sealed to better isolate the vessel acoustically, thus reducing undesirable effects related to the infiltration of exterior acoustic noise sources, which may affect optical breakdown and/or subsequent modifications to the generated acoustic shockwave. The vessel 1300 may also be isolated optically (e.g., its walls may be opaque at laser wavelengths) to reduce exposure to direct or stray light from the light source 1100, which can be a safety hazard for users and/or vegetation and animals in the environment surrounding the optical breakdown acoustic transducer 1000. The vessel 1300 may be rated to satisfy laser-safety requirements for applications involving human operators and/or imaging targets.

The vessel 1300 can also include an optical window between the cavity and the light source 1100 to transmit light from the light source 1100 to the fluid 1400 contained in the cavity of the vessel 1300. The optical window can be formed from materials that are transparent to the light emitted by the light source 1100 including but not limited to glass and various plastics. In some instances, the optical window may be an optical element 1200 such as a condenser lens, aperture, or phase plate. Additionally, the interior walls of the cavity may be shaped and/or textured to reduce coherent reflections of light within the fluid during operation.

The vessel 1300 can also include an acoustic outlet 1500 to transmit the acoustic shockwave generated within the cavity of the vessel 1300 into the surrounding medium for subsequent use. The acoustic outlet 1500 may be formed from a material having a substantially similar acoustic impedance to the fluid 1400 and/or the medium surrounding the optical breakdown acoustic transducer 1000 (e.g., seawater for ocean applications). In instances where the fluid 1400 is substantially different from the surrounding medium, the acoustic outlet 1500 may have a variable acoustic impedance to increase overall acoustic wave transmission between the two fluids (e.g., a gradient in acoustic impedance). The acoustic outlet 1500 may be formed on at least a portion of the vessel 1300. For example, the acoustic outlet 1500 may be at least one side of the vessel 1300, an acoustic lens, or an acoustically transparent window. In some instances, the vessel 1300 maybe substantially formed from an acoustically transparent material such that a substantial portion of the vessel 1300 is the acoustic outlet 1500. For example, the optical breakdown acoustic transducer 1000 can function as an acoustic point source for each breakdown site present in the cavity.

The acoustic outlet 1500 can also be used to modify the shape of the generated acoustic shockwave. For instance, the acoustic outlet 1500 may be shaped (e.g., with a convex curvature) to collimate or focus the acoustic shockwave towards a particular location relative to the optical breakdown acoustic transducer 1000. For a spherical acoustic shockwave generated from a single breakdown site, the acoustic outlet 1500 may have a focal point positioned coincident with the breakdown site such that the acoustic outlet 1500 collimates the spherical acoustic shockwave. The acoustic outlet 1500 can also have a more complex shape to modify the wave front of the acoustic shockwave. For example, the acoustic outlet 1500 may be shaped such that the acoustic shockwave is focused towards multiple positions in the surrounding medium. The acoustic outlet 1500 may be other various types of acoustic elements including, but not limited to a shaped higher-impedance medium, a tunable fluid-filled pouch, a diffractive multi-material element, or other suitable device. The acoustic outlet 1500 can also be used to hermetically seal the cavity of the vessel 1300.

The fluid 1400 provides the medium where optical breakdown and generation of acoustic shockwaves occur. The fluid 1400 may be chemically different from the fluid surrounding the optical breakdown acoustic transducer 1000. Various fluids may be used including, but not limited to water, doped water, oils, polymers, gels, inorganic solvents, or any other gas or liquid with a suitable breakdown threshold, low attenuation at the laser wavelength, and low attenuation at the desired acoustic frequencies. For example, the fluid 1400 may be purified water, silicone oil, isopropyl alcohol, or glycerol. Dopants in the fluid 1400 may include salts that dissociate (e.g., NaCl, KCl) or micro- and nano-particles that function as solid breakdown sites in the fluid 1400. The fluid 1400 may be substantially immune or substantially resistant to irreversible changes in its chemistry or properties after high-temperature cycling. The fluid 1400 may also be doped to change the irradiance threshold such that optical breakdown can more readily occur at lower optical pulse powers/energies, to increase the efficiency of optoacoustic conversion, and/or to increase acoustic transmission to the medium surrounding the optical breakdown acoustic transducer 1000. For example, sea water can exhibit an irradiance threshold approximately six times lower than pure water because of dissociated ion and dissolved gas content. This can enable the cavity/transducer head to operate with a higher efficiency of external transduction, so it transmits more sound for a given input energy.

The acoustic and optical properties of the fluid 1400 may also be tuned by varying the fluid pressure of the fluid 1400 when contained within the cavity of the vessel 1300. This tunability can be used to adjust various aspects of the breakdown process. For instance, low fluid pressures may reduce the irradiance threshold, thus increasing the generation of cavitation bubbles/shock waves. When operated at such low pressures, the cavity can be designed to reduce the likelihood of shockwaves producing cavitation on or damaging any of the walls or optics. High fluid pressures may be used to generate higher amplitude acoustic waves, but may increase the irradiance threshold for light to cause optical breakdown. The mechanical design of the cavity and the properties of the fluid 1400 may set limits on the fluid pressure. For example, at a particular temperature, the fluid pressure should be sufficiently high such that the fluid 1400 doesn't vaporize and the fluid pressure should be sufficiently low such that the fluid 1400 doesn't solidify. For instance, at room temperature (300 K), the fluid pressures for water can range between about 5 kPa to about 1 GPa while remaining in the liquid phase.

The cavity of the vessel 1300 may be substantially filled with the fluid 1400 to reduce the presence of air bubbles, which can cause optical and acoustical coupling losses. This can be accomplished by submerging the cavity in a bath of the fluid 1400. In this manner, air bubbles in the cavity of the vessel 1300 can be substantially removed. The cavity may then be roughly sealed while submerged in the bath of the fluid 1400 followed by a final hermetic sealing thereafter. The temperature and pressure of the bath of fluid 1400 can help to seal the cavity by forming a partial vacuum within the cavity upon cooling down from an elevated temperature (e.g., similar to the heating process used to jar and pickle vegetables). The cavity can also have an end cap (e.g., for the optics assembly or acoustic lens) that can couple to the vessel 1300 via a screw threads. The cavity can be filled with fluid 1400 above the screw threads such that when the end cap is coupled to the vessel 1300, a slight overpressure is applied to the fluid 1400 in the cavity.

The light source 1100 may be one or multiple high-powered pulsed laser that can generate multiple optical pulses that can each cause breakdown of the fluid 1400. The optical pulses can be repeated and modulated temporally (e.g., at kHz rates) to create a time-modulated acoustic source. A modulated source can be used in applications including, but not limited to communications encoding and time-encoded imaging/sensing sources. The light source 1100 may be various types of lasers including, but not limited to chemical lasers, gas lasers, solid-state lasers, or any combination thereof. The light source 1100 may emit optical pulses with a pulse duration ranging between about 1 picosecond to about 1 millisecond, a peak pulse power ranging between about 100 watts to about 1 gigawatt, and a wavelength ranging between 200 nm to 2000 nm. In some instances, a preferred pulse duration can be about 1 nanosecond, a preferred peak pulse power can be about 1 gigawatt, and a preferred wavelength about 532 nm. However, the preferred pulse duration and peak pulse power may also depend on the laser wavelength and other properties of the fluid 1400 and/or the optical element 1200.

Typically, higher energy photons (e.g., visible to ultraviolet regimes) can more efficiently induce optical breakdown. However, in some instances, infrared photons can also be used to induce breakdown for specially formulated fluids 1400. For example, the light source 1100 may emit pulses at short excitation wavelengths (e.g., about 250 nm). If the pulses are focused down to a diffraction-limited spot size, the necessary peak pulse power can be as low as 10 W. In another example, the light source 1100 may be a Nd:YAG laser configured to emit a pulsed laser beam at a wavelength of about 532 nm (e.g., via a frequency doubling crystal). For the Nd:YAG laser, the preferred pulse duration can range between about 0.1 ns to about 100 ns and the peak pulse power can range between about 0.5 kW to about 100 MW at a focused spot size ranging between about 1 μm to about 1 mm.

The optical element(s) 1200 can be used to shape the optical beam generated by the light source 1100 to control the breakdown of the fluid 1400. At least one optical element 1200 may be used having at least one focal point. Light emitted from the light source 1100 can thus be directed through the optical element 1200 to focus the light down to a sufficiently small spot size where the resultant irradiance exceeds the irradiance threshold of the fluid 1400 to induce breakdown. In some instances, multiple optical element(s) 1200 may be used to improve shaping of the optical beam such that a smaller focus can be achieved. For example, the optical beam from the light source 1100 may be expanded in size by a first optical element (e.g., the beam diameter increases by a factor of 10) and then focused to a point by a second optical element having a focal point located in the fluid-filled cavity to induce breakdown. Generally, the spot size of an optical beam focused by an optical element is inversely proportional to the diameter of the optical beam entering the optical element; hence, the reason for first expanding the optical beam.

Beam Shaping Optics for an Optical Breakdown Acoustic Transducer

Figure 2:
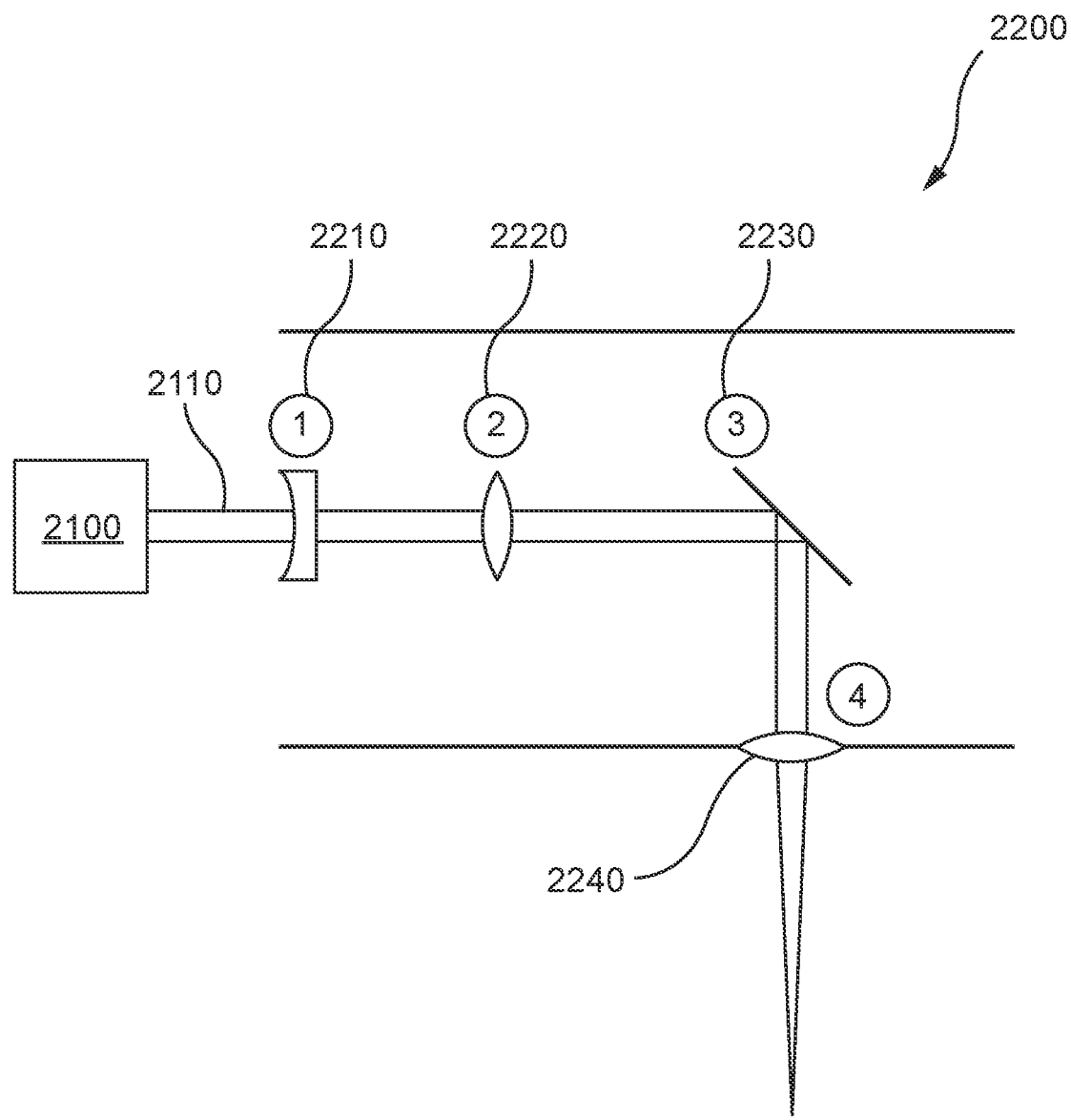
FIG. 2 is an illustration of an exemplary optical assembly with a light source and multiple optical elements to generate and focus an optical beam.

FIG. 2 shows an exemplary assembly of optical elements 2200 used to modify the shape and size of the optical beam from the light source 2100 in an optical breakdown acoustic transducer. As shown, an incident optical beam 2110 is expanded in size through a first lens 2210 (e.g., a plano-concave or bi-concave lens) and is then subsequently collimated by a second lens 2220 (e.g., a bi-convex lens). The optical beam 2110 is then reflected off of a mirror 2230 towards a condensing lens 2240, which focuses the optical beam 2110. The focal point of the condensing lens 2240 is located in a cavity of a vessel containing fluid; breakdown occurs at the focal point. In some instances, the mirror 2230 may be substituted by other reflective elements including, but not limited to a static phase mask, a reflective phase mask, a phase plate, a reflective amplitude mask, and a digital micromirror device. More sophisticated reflective elements can be used to shape the optical beam 2110 to have more complex wave fronts (e.g., varying the shape and size of the breakdown site, creating multiple breakdown sites). Additionally, the optical beam can be focused to a beam spot size with various shapes to affect the source shape of the acoustic waves. For example, the optical beam may be focused to a point, a line, or a small area to produce a corresponding point source (e.g., spherical acoustic wave), line source (e.g., cylindrical acoustic wave), and area source.

The optical element(s) 2200 may be static such that the focal points remain fixed in position within the cavity during operation. Alternatively, the optical elements 2200 may include dynamically adjustable components that can actively modify the shape and/or directionality of the optical beam. Dynamically adjustable components can include, but are not limited to an SLM (e.g., a reflective SLM in place of the mirror 2230), an adaptable lens (e.g., a liquid, electrochromic, or liquid-crystal lens), a motorized optical attenuator, and a digital micromirror device. These dynamically adjustable components can be used to adjust the shape and size of the optical beam as well as the wave front along at least one spatial dimension. In particular, the SLM can shape the spatial wave front of the optical beam such that the position of the breakdown site is moved relative to the optical elements 2200 and/or the acoustic outlet, enabling multiple operating modes. For example, if the acoustic outlet is an acoustic lens having a focal point, by moving the breakdown site closer to or away from the acoustic outlet, the acoustic shockwave coupled to the surrounding environment can transition from being collimated, focusing, or diverging.

In another example, the SLM can be used to form multiple breakdown sites within the fluid. For instance, the SLM can change the directionality of a single optical beam at a sufficiently fast rate such that multiple breakdown sites are formed in a substantially simultaneous manner (e.g., the SLM can move a single breakdown site at a velocity exceeding the speed of sound of the fluid). In another instance, the SLM can produce an optical beam having a wave front that forms multiple focal points in the fluid when passing through a subsequent optical element (e.g., a condenser lens). The formation of multiple breakdown sites can allow for more complex acoustic wave fronts, such as beamforming as produced by phased array devices for SONAR or medical ultrasound. For example, by adjusting the phase and amplitude of the acoustic shockwaves generated at each breakdown site, an acoustic beam can be formed outside of the optical breakdown acoustic transducer, which can then be directed to different locations in the surrounding environment (e.g., at variable distance and angle) without having to physically move the optical breakdown acoustic transducer. The acoustic beam can also have variable wave fronts (e.g., focusing, planar).

Sensors and Modulators for Monitoring and Adjusting Acoustic Shockwaves

The optical breakdown acoustic transducer can also include various sensors to detect and characterize the breakdown of the fluid and the subsequent generation of an acoustic shockwave. For example, one or more acoustic receivers may be used to measure the amplitude of at least a portion of the acoustic shockwave as a function of time. Various types of acoustic receivers may be used including, but not limited to piezoelectric elements and magnetostrictive elements. The acoustic receivers can be disposed proximate to the breakdown site within the cavity of the vessel and/or proximate to the exterior of the vessel, preferably near the acoustic outlet. Based on the geometric arrangement of the one or more acoustic receivers and their relative position to the breakdown site, the amplitude of the acoustic shockwave can be calculated at various positions (e.g., a distance and an angle from the acoustic outlet) from the optical breakdown acoustic transducer as a function of time. The acoustic receivers can thus be used to calibrate the optical breakdown acoustic transducer such that users can determine the amount of acoustic energy delivered to a particular position in the media where the optical breakdown acoustic transducer is deployed.

In another example, one or more optical sensors can be used to monitor various aspects of the breakdown process including, but not limited to the breakdown geometry (e.g., imagery), plasma emission (e.g., intensity, spectroscopy), bubble formation (e.g., imagery) as a function of time. Various types of optical sensors may be used including, but not limited to a photodiode, a spectrometer, a camera, and an optical vibrometer. The optical sensors may be disposed within the cavity of the vessel or proximate to an optical window with a field of view of the breakdown site. In some instances, the one or more optical sensors may include a combination of a laser (e.g., a laser diode) and a photodiode arranged as an optical vibrometer to measure acoustic wave properties based on the vibrations of a surface in the optical breakdown acoustic transducer. For example, the surface may be an optical window or another elastic material having an optically reflective surface. The data collected by the optical sensors can be applied as input into known relationships that correlate the optical and acoustic behavior of breakdown in order to calculate the strength of the acoustic shockwave (e.g., amplitude of acoustic wave when initially generated). The optical sensors can be used to calibrate the optical breakdown acoustic transducer such that adjustments to the light source and the optical elements 1200 during operation can generate acoustic shockwaves with a predictable amplitude.

In some instances, the acoustic receivers and/or the optical sensors may be used in an active feedback loop where adjustments are made to the optical breakdown acoustic transducer to generate an acoustic beam that meets a desired metric. The desired metric can include, but is not limited to an acoustic amplitude, an acoustic waveform, a spatial radiation pattern, and any combination thereof. Data measured by the various sensors can be used to actively adjust various control parameters of the optical breakdown acoustic transducer to meet the desired metric including, but not limited to the laser power output, the optical pulse duration, the optical pulse period, the orientation of one or more mirrors, the state of an SLM, and any combination thereof. The active feedback loop may operate in a real-time manner. For example, the time used to measure data with various sensors and adjust various control parameters for a single iteration of the active feedback loop can range between about 1 ms to about 60 s.

The optical breakdown acoustic transducer can also include additional optical and acoustic sources that modify the properties of the fluid to control various aspects of the breakdown process and the subsequent propagation of an acoustic shockwave. For example, a subset of the multiple optical pulses, referred to as the seed optical pulses, generated by the light source or one or more secondary light sources can be used to seed one or more breakdown sites to improve the efficiency and effectiveness of generating a breakdown plasma and subsequent acoustic shockwave. For example, the seed optical pulses may alter the electron state of the fluid to produce a stronger and/or more consistent plasma for a fixed laser pulse. The seed optical pulses may have a lower peak pulse power where each one of the optical pulses provides an irradiance just below the irradiance threshold. A subsequent optical pulse having a peak pulse power below or above the irradiance threshold can then be transmitted following the seed optical pulses to induce breakdown. In this manner, the acoustic output can be tuned, made more consistent from one laser pulse to the next, and peak pulse power requirements of the light source can be reduced on a per pulse basis.

In another example, an acoustic transducer can be implemented into the optical breakdown acoustic transducer. For instance, the acoustic transducer may be an acoustic modulator. The acoustic modulator may be an ultrasonic transducer (e.g., a single resonant crystal, one or more piezoceramic elements) disposed within the cavity of the vessel. The acoustic modulator can generate a pressure distribution within the fluid of the cavity to modify various aspects of the breakdown process and/or the acoustic shockwave after generation including, but not limited to the frequency content, directionality, and amplitude of the generated acoustic shockwave. For instance, the acoustic modulator can produce standing ultrasonic fields that amplify a particular frequency or frequency band of the acoustic shockwave. In another instance, the acoustic modulator can generate higher or lower pressures within the fluid, thus changing the concentration of dissolved gasses or other additives in the fluid, which could then alter the irradiance threshold for breakdown and/or the optical-acoustic conversion efficiency.

As described above, the optical breakdown process can be used to generate acoustic shockwaves having a large bandwidth while simultaneously having a high amplitude. In some applications, the large bandwidth acoustic beams produced by the optical breakdown acoustic transducer can be used for acoustic spectroscopy and/or multispectral imaging. For example, the optical breakdown acoustic transducer can direct an acoustic beam towards a sample disposed proximate to the optical breakdown acoustic transducer. An acoustic detector can measure an acoustic signal from the sample (e.g., acoustic wave reflection or transmission) as a function of time. The measured temporal acoustic signal of the sample can then be transformed from a time domain representation to a frequency domain representation via an operation such as a Fast Fourier Transform (FFT). The frequency spectra of the sample can provide information on the sample including the material composition, dimensions, and the shape of the sample.

In instances where the optical breakdown acoustic transducer can move the acoustic beam to various locations on the sample, a multispectral image can be generated where the resolution of the image is dictated by the number of locations and their arrangement where an acoustic signal is measured. For example, a multispectral image can be measured along a 128 by 128 grid where the dimensions of each pixel can vary based on the physical distance between adjacent locations on the sample. Multispectral images can be used in several applications including, but not limited to forming material maps of a sample composed of materials and/or morphologies having different acoustic properties, tomographic reconstruction of the sample geometry based on reflected and/or transmitted acoustic waves, and characterization of the frequency response of an acoustic resonator.

Generally, the bandwidth of the acoustic shockwave, and hence the frequency content contained therein, is, in part, dependent on the irradiance of the optical pulse used to induce breakdown. By varying the intensity of the optical pulse, different frequencies or frequency bands can be amplified or suppressed in the acoustic shockwave. In view of the applications described above, the optical breakdown acoustic transducer can also be operated where particular frequencies spanning a large frequency range (e.g., 1 kHz to 100 MHz) can be preferentially excited to facilitate characterization of a sample at known frequencies of interest.

A Collimated Acoustic Beam from an Optical Breakdown Acoustic Transducer

Figure 3A:
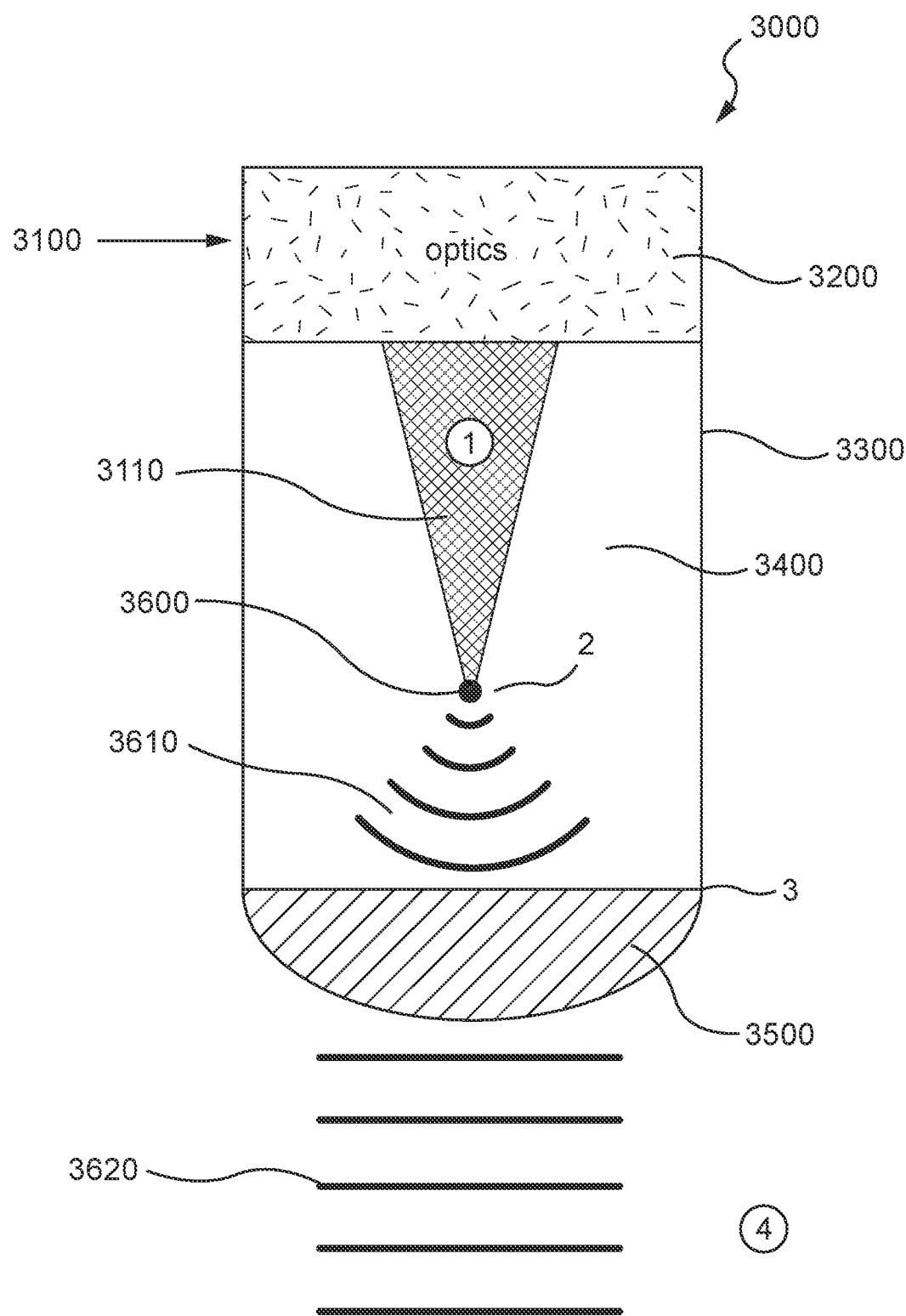
FIG. 3A is an illustration of an exemplary optical breakdown acoustic transducer that generates a collimated acoustic beam via optical breakdown from a single focal point.
Figure 3B:
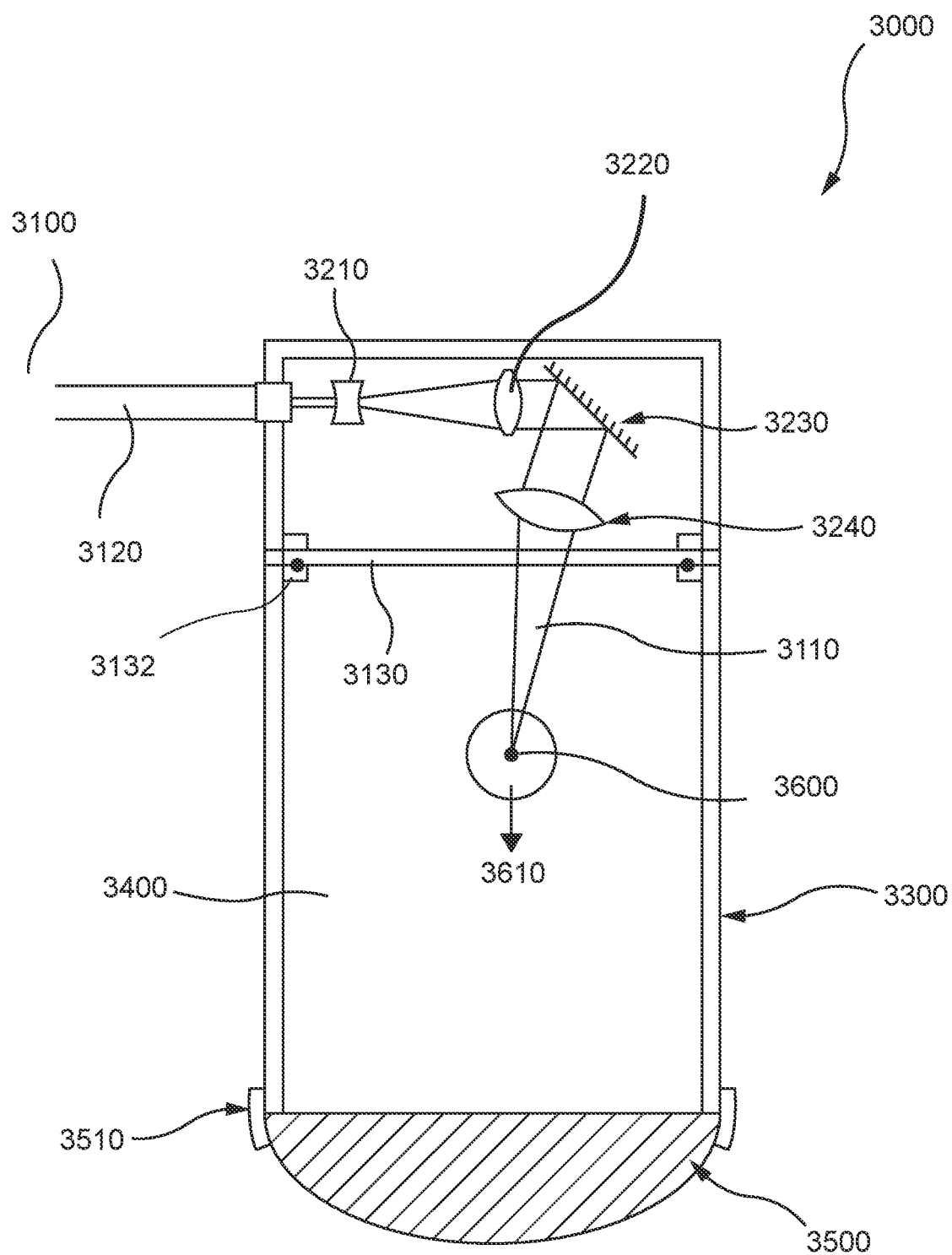
FIG. 3B is a detailed cross-section of the optical breakdown acoustic transducer of FIG. 3A.

FIGS. 3A and 3B show an exemplary realization of an optical breakdown acoustic transducer 3000 that generates a collimated acoustic beam 3620. As shown in FIG. 3A, the optical breakdown acoustic transducer 3000 can receive an optical beam 3110 from a light source 3100 located separately from the vessel 3300. The vessel 3300 can have two cavities, the first cavity containing optical elements 3200 to shape the optical beam 3110 and the second cavity containing a fluid 3400. The optical beam 3110 can be focused to a breakdown site 3600 (e.g., a focal point of the optical elements 3200), from which a spherical acoustic shockwave 3610 propagates within the fluid 3400 in the cavity defined by the vessel 3300. The acoustic wave 3610 is then collimated by an acoustic outlet 3500 (also referred to as an acoustic lens 3500), which then propagates out for communication or sensing as a collimated beam 3620.

FIG. 3B shows a detailed cross-sectional view of the optical breakdown acoustic transducer 3000 shown in FIG. 3A. As shown, the optical beam 3110 may be received by the optical breakdown acoustic transducer 3000 via an optical fiber 3120 coupled to the light source 3100. The optical elements 3200 can include an expansion lens 3210, a collimating lens 3220, a mirror 3230, and a condenser lens 3240 to improve focusing while maintaining a compact arrangement. An optical window 3130 may be disposed between the first compartment containing the optical elements 3200 and the cavity containing the fluid 3400. The optical window 3130 may be coupled to the vessel 3300 via lip and gasket/O-ring seal 3132. The acoustic lens 3500 may be a separable component that is coupled to one end of the vessel 3300 via a seal 3510 disposed around the periphery of the acoustic lens 3500.

An Optical Breakdown Acoustic Transducer with Multiple Breakdown Sites

Figure 4A:
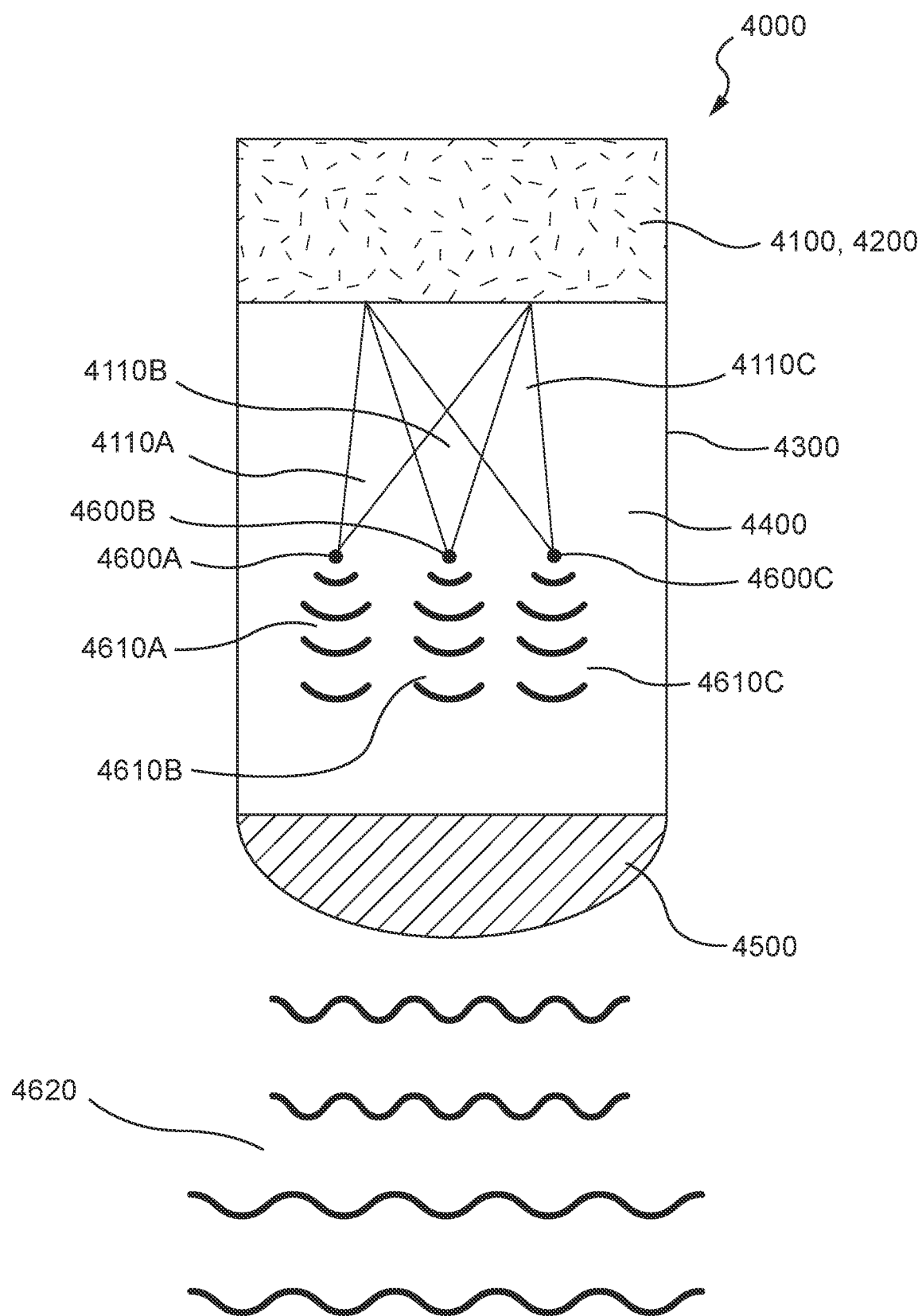
FIG. 4A is an illustration of an exemplary optical breakdown acoustic transducer that generates an acoustic beam having a reconfigurable wave front via optical breakdown from multiple focal points.
Figure 4B:
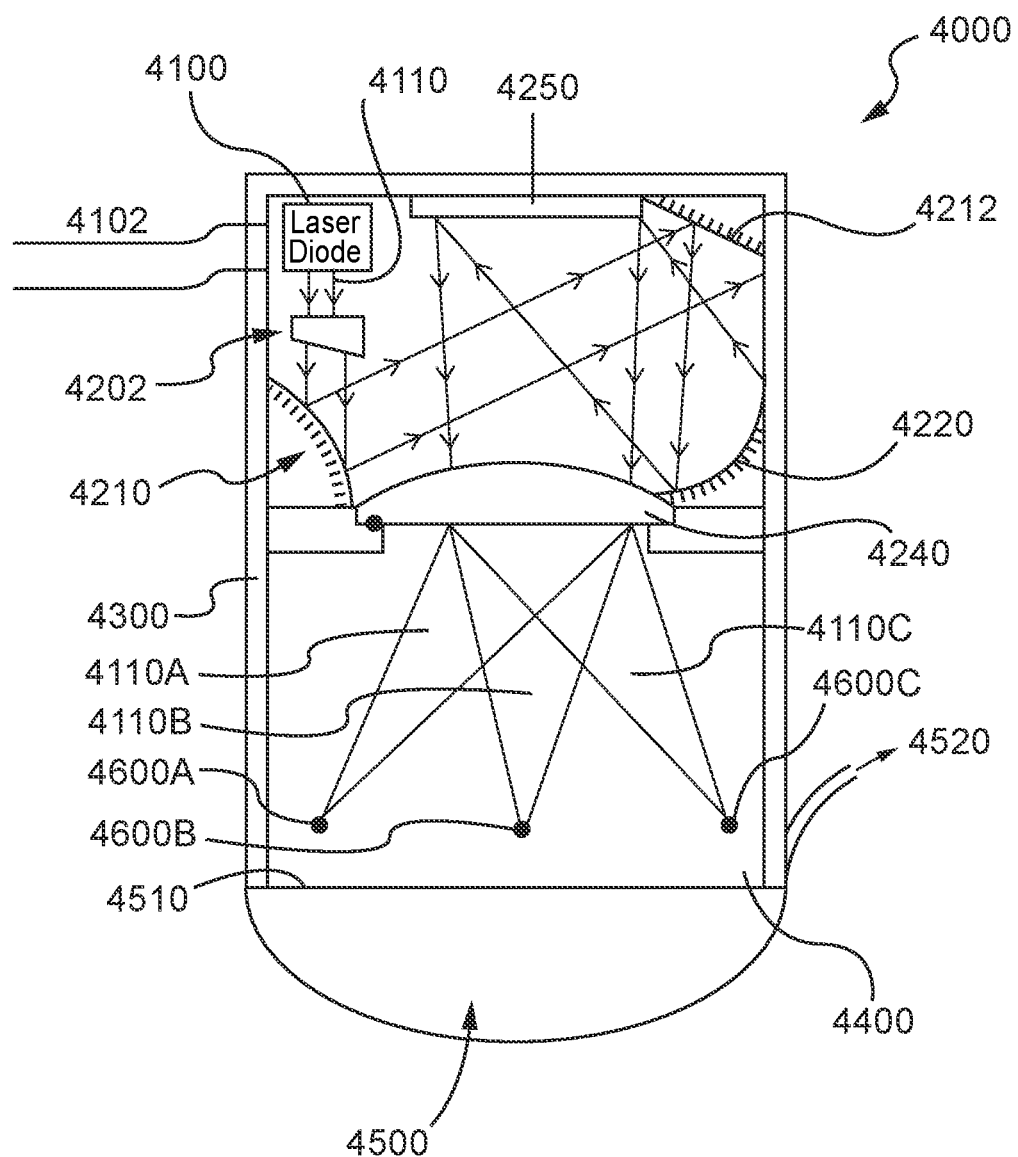
FIG. 4B is a detailed cross-section of the optical breakdown acoustic transducer of FIG. 4A.

FIGS. 4A and 4B show another exemplary optical breakdown acoustic transducer 4000 that can form three breakdown sites 4600A, 4600B, and 4600C, producing an acoustic beam 4620 with a complex wave front. As shown in FIG. 4A, the optical breakdown acoustic transducer 4000 can include a vessel 4300 having two cavities. The first cavity can contain a light source 4100 that emits an optical beam 4110 and optical elements 4200 to shape the optical beam 4110. The optical elements 4200 can shape the optical beam such that three separate optical beams 4110A, 4110B, and 4110C are formed. The second cavity of the vessel 4300 can contain a fluid 4400. The optical beams 4110A-4110C may be focused at breakdown sites 4600A-4600C in the fluid 4400, producing three acoustic shockwaves 4610A, 4610B, and 4610C. The acoustic waves 4610A-4610C can then be superimposed onto one another and transmit through an acoustic outlet 4500 (also referred to as an acoustic lens 4500), producing an acoustic beam 4620 with a desired wave front.

FIG. 4B shows a more detailed cross-sectional view of the optical breakdown acoustic transducer 4000 shown in FIG. 4A. As shown, the light source 4100 can be a diode laser with electrical connections 4102 for power and control fed through the vessel 4300. The optical elements 4200 can include (1) a beam-correction prism 4202 to adjust the shape of the optical beam 4110 emitted by the light source 4100, (2) a curved expansion mirror 4210, a flat mirror 4212, and a curved collimating mirror 4220 to modify the size and divergence of the optical beam, (3) a SLM 4250 to generate an optical beam with a complex wave front, and (4) a condenser lens 4240 that directs the optical beam into three distinct focal points 4600A-4600C as a result of the complex wave front. The condenser lens 4240 can also function as an optical window coupling the first compartment to the cavity of the vessel 4300. The acoustic lens 4500 can be a shape-changeable lens filled with a liquid that can be pumped into or out of the acoustic lens 4500 via a pump and liquid reservoir 4520. The acoustic lens 4500 can be coupled to the vessel 4300 via a seal 4510 disposed along the periphery of the acoustic lens 4500.

Figure 4C:
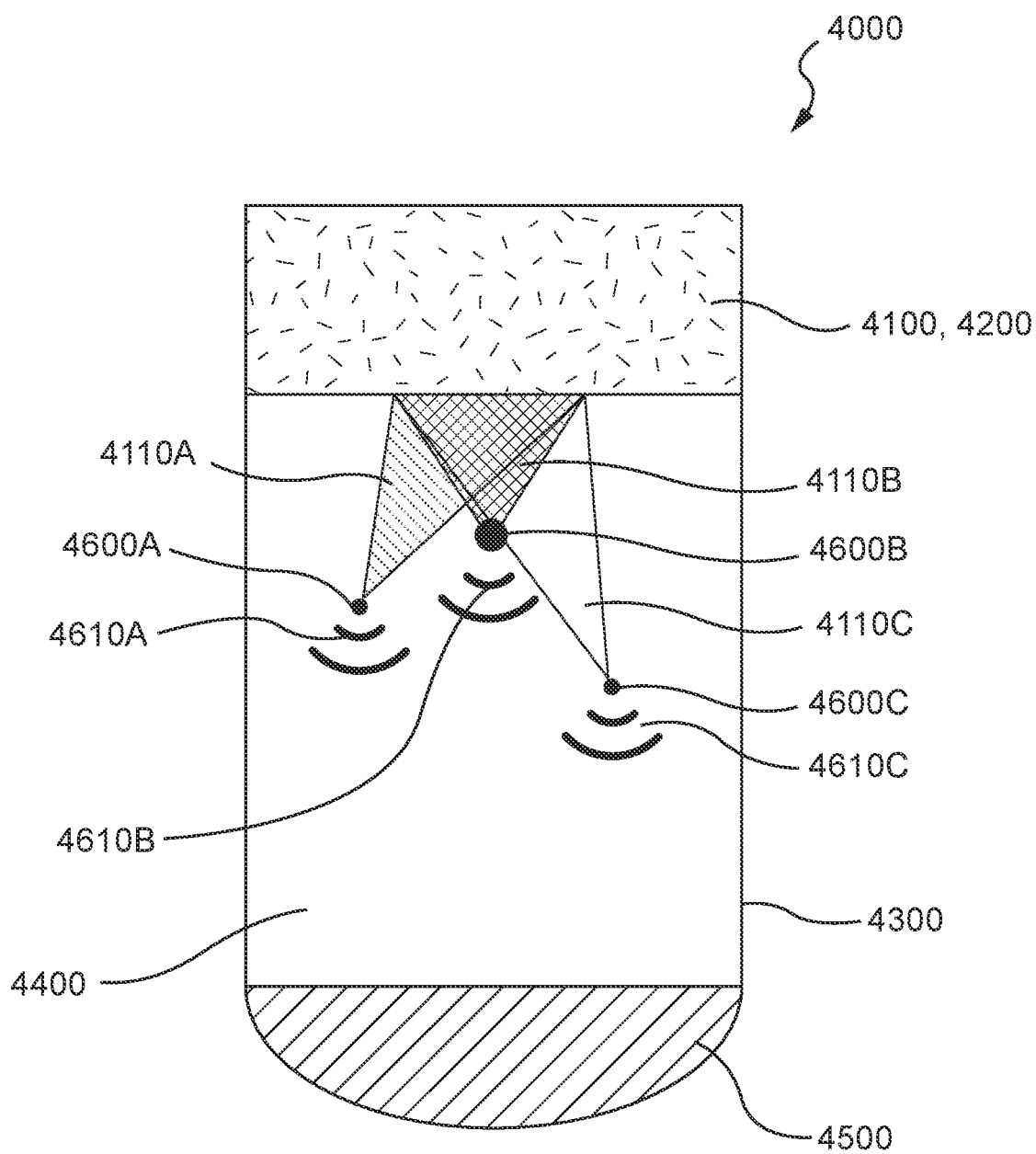
FIG. 4C is an illustration of the optical breakdown acoustic transducer of FIG. 4A showing multiple breakdown sites having different acoustic properties.

FIG. 4C shows another illustration of the optical breakdown acoustic transducer 4000 shown in FIG. 4A for a case where the breakdown sites 4600A-4600C are located at different positions in the fluid 4400 and tuned to emit acoustic shockwaves 4610A-4610C that each have distinct acoustic properties. As shown, the power of each optical beam 4110A-4110C can be independently varied such that the amplitude of the resultant acoustic shockwaves 4610A-4610C can have different amplitudes. In other instances, the frequency content of each acoustic shockwave 4610A-4610C can also be tuned by varying the power of each optical beam 4110A-4110C. In this manner, acoustic beams having a complex acoustic wave front can be generated by the optical breakdown acoustic transducer 4000. For example, the frequency content of each acoustic wave 4610A-4610C can be tuned to amplify different frequencies to produce a spatially-varying chirped acoustic pulse.

A Miniaturized Optical Breakdown Acoustic Transducer

Figure 5:
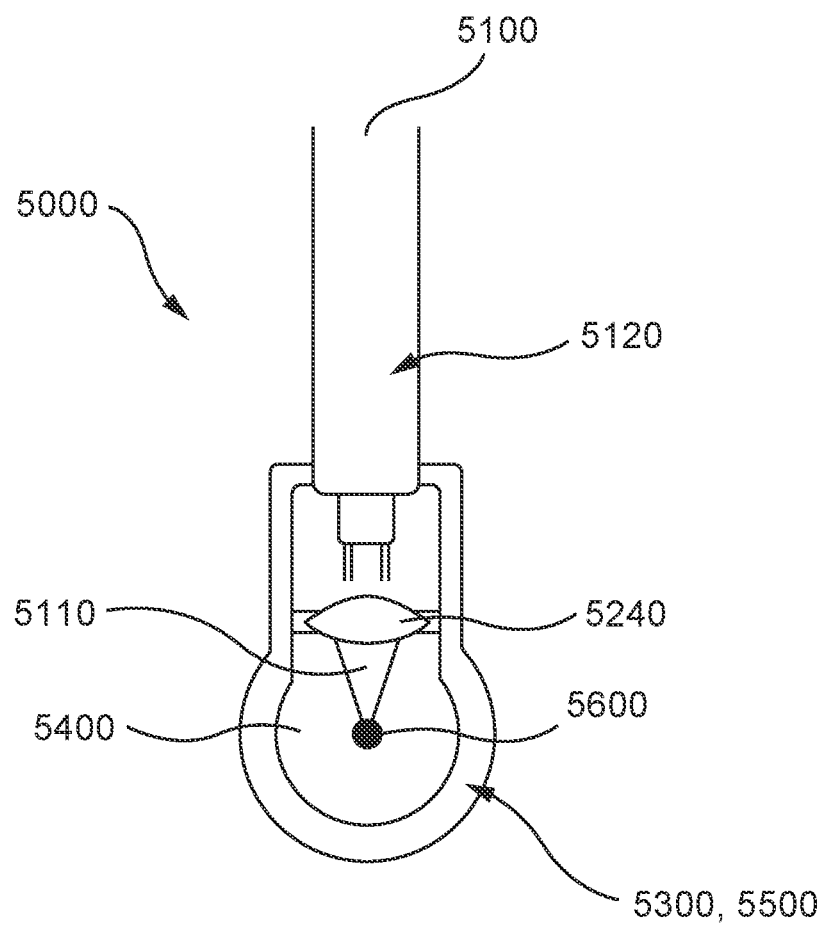
FIG. 5 is an illustration of an exemplary compact optical breakdown acoustic transducer suitable for mounting on the distal end of an endoscope or optical fiber.

FIG. 5 shows yet another exemplary optical breakdown acoustic transducer 5000, which may be disposed on a tip of a miniaturized device such as an endoscope. As shown, an optical fiber 5120 may be used to couple a light source 5100 to a vessel 5300. Upon outcoupling form the optical fiber 5120, the optical beam 5110 is directed to a condenser lens 5240, which focuses the optical beam 5110 to a breakdown site 5600 located within a sealed cavity of the vessel 5300 containing fluid 5400. The condenser lens 5240 also functions as an optical window. The focused optical beam 5110 causes breakdown of the fluid 5400 at the breakdown site 5600, thus generating an acoustic shockwave that propagates as a spherical wave towards the walls of the vessel 5300. The portion of the walls of the vessel 5300 surrounding the cavity may be substantially spherical and can also function as an acoustic outlet 5500. Thus, the acoustic shockwave can couple into the surrounding media as a substantially spherical wave. In this manner, the optical breakdown acoustic transducer 5000 can be used to produce a spherical acoustic source.

An Optical Breakdown Acoustic Transducer with Acoustic Receivers

Figure 6:
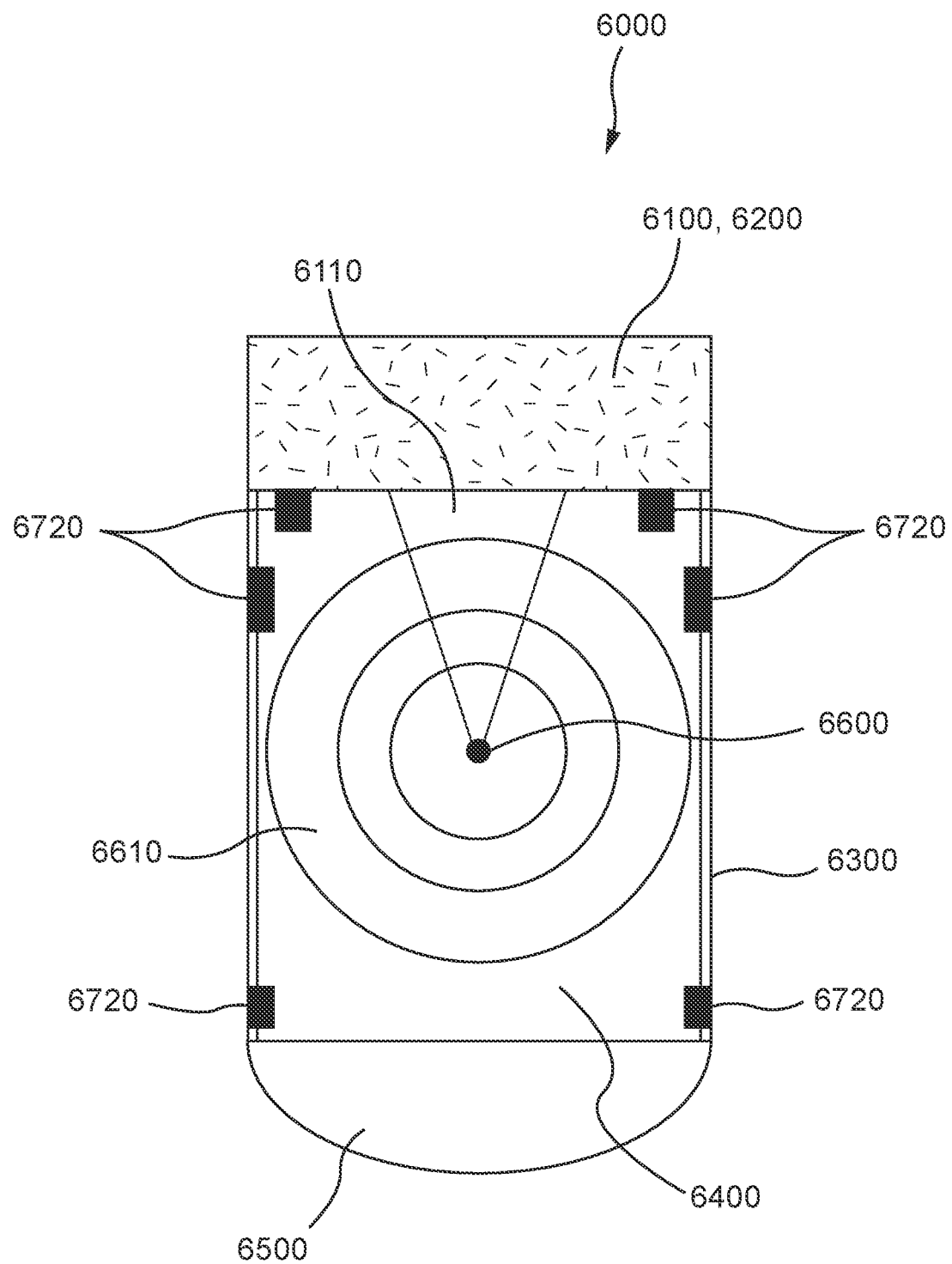
FIG. 6 is an illustration of an exemplary optical breakdown acoustic transducer that includes multiple acoustic receivers to monitor the properties of an acoustic shockwave.

FIG. 6 shows another exemplary optical breakdown acoustic transducer 6000 that includes a plurality of acoustic receivers 6720 disposed in the cavity of a vessel 6300 containing fluid 6400. As shown, a light source 6100 in combination with optical elements 6200 can emit and focus an optical beam 6110, respectively, at a breakdown site 6600 to produce an acoustic wave 6610. The acoustic wave 6610 may be a substantially spherical or a substantially cylindrical wave. An acoustic outlet 6500 disposed at one end of the vessel 6300 can be used to couple the acoustic wave 6610 out into at least a portion of the surrounding medium. Multiple acoustic receivers 6720 may be disposed in the fluid 6400 around the breakdown site 6600 to measure the pressure amplitude of the acoustic wave 6610 as a function of time.

If the location of each one of the multiple acoustic receivers 6720 are known relative to each other and/or the vessel 6300, the data measured by the multiple acoustic receivers 6720 can be used to calculate the position of the breakdown site 6600 in the vessel 6300 and/or the amplitude of the acoustic shockwave 6610 at any location within the cavity of the vessel 6300. Furthermore, if the acoustic outlet 6500 is calibrated such that it's shape, dimensions, and orientation with respect to the vessel 6300 are known, the data measure by the multiple acoustic receivers 6720 may also be used to determine the shape, directionality, and amplitude of the acoustic beam coupled into the surrounding medium.

An Optical Breakdown Acoustic Transducer with Optical Sensors

Figure 7:
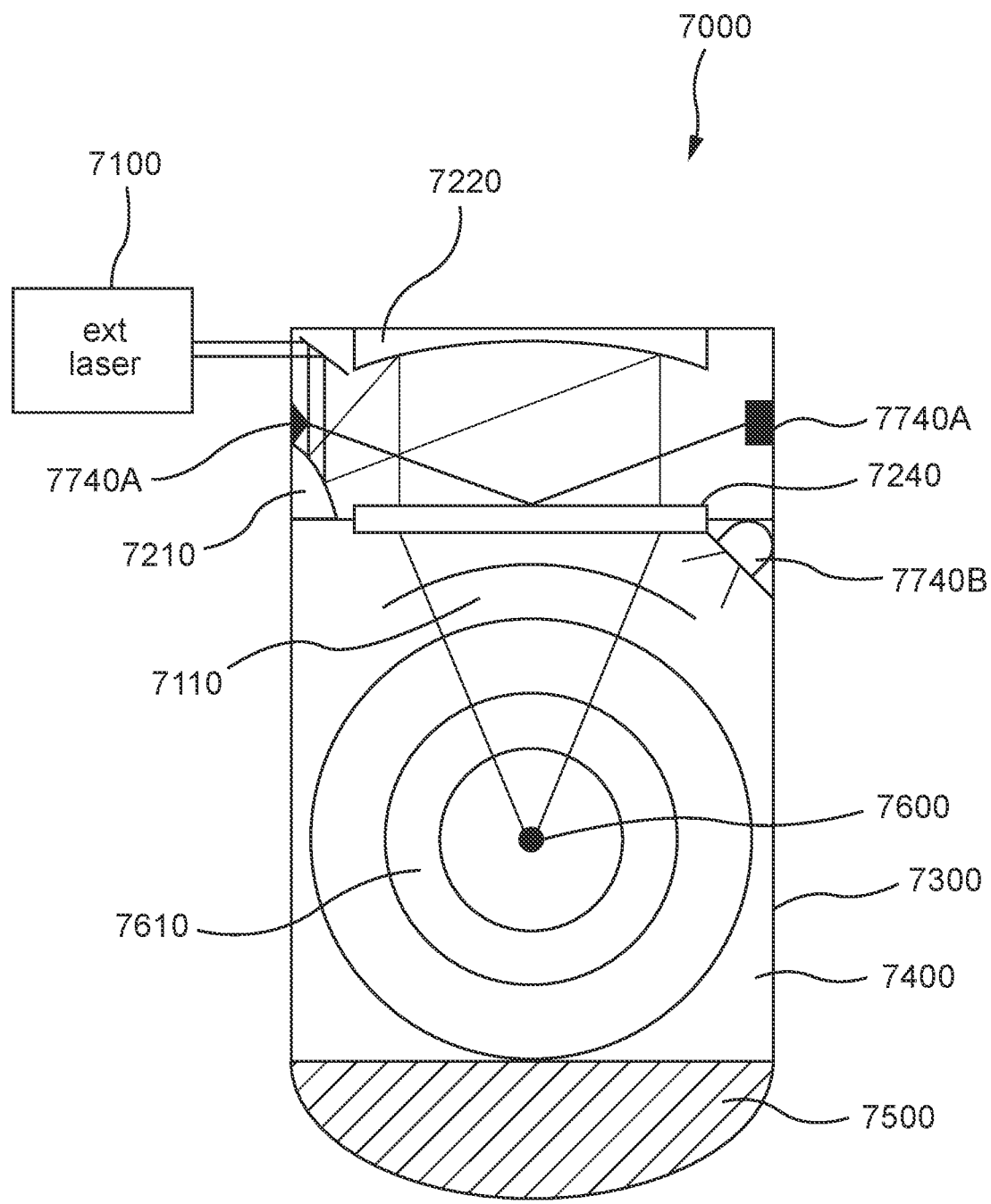
FIG. 7 is an illustration of an exemplary optical breakdown acoustic transducer that includes multiple optical sensors to monitor the properties of a breakdown process and an acoustic shockwave resulting from the breakdown process.

FIG. 7 shows another exemplary optical breakdown acoustic transducer 7000 that includes optical sensors 7740A and 7740B to monitor the breakdown process and characterize the properties of the acoustic wave 7610 generated by breakdown. As shown, a vessel 7300 may have two cavities. A light source 7100 that emits an optical beam 7110 may be disposed externally to a vessel 7300 and configured to be in optical communication with the first cavity of the vessel 7300. The optical beam 7110 can then be shaped by various optical elements including a curved beam expansion mirror 7210, a curved collimating mirror 7220, and a condenser lens 7240. The optical beam 7110 is focused at a breakdown site 7600 located in the second cavity of the vessel 7300, which is substantially filled with a fluid 7400. Breakdown occurs at the breakdown site 7600, resulting in the generation of an acoustic shockwave 7610 that couples to at least a portion of the surrounding medium via an acoustic outlet 7500.

In the first cavity, the optical sensor 7740A may be a combination of a laser diode and a photodetector that functions as an optical vibrometer. The laser diode may emit an optical beam towards a surface that is acoustically coupled to the second cavity and then reflected onto the photodetector. Vibrations at the surface due to the acoustic wave 7610 will cause a Doppler shift in the reflected optical beam. The Doppler shift can be detected by the photodetector and correlated to an amplitude and frequency(s) of the acoustic wave 7610. For instance, in FIG. 7, the laser diode illuminates and reflects off the condenser lens 7240 and onto the photodetector. The laser diode 7740 may illuminate the surface at a sufficiently high angle of incidence to increase the Doppler shift, thus increasing the sensitivity to vibrations. In another instance, the photodetector may instead be a position sensing detector (e.g., a photodetector with two or four active photodiode portions). As the surface vibrates, the position of the reflected optical beam on the position sensing detector may change. Thus, the change in position detected by the position sensing detector can be correlated to an amplitude and frequency(s) of the acoustic wave 7610.

In the second cavity, the optical sensor 7740B may be a photodiode or a miniaturized spectrometer that monitors various optical characteristics of breakdown including, but not limited to the plasma duration, emission spectra, and emission power. In some instances, the optical sensor 7740B may have a sufficiently wide field-of-view (FOV) such that if the breakdown site 7600 is moved (e.g., by a SLM), the resultant plasma created at the breakdown site 7600 during breakdown remains within the FOV of the optical sensor 7740B.

An Optical Breakdown Acoustic Transducer with Acoustic Transducers

Figure 8:
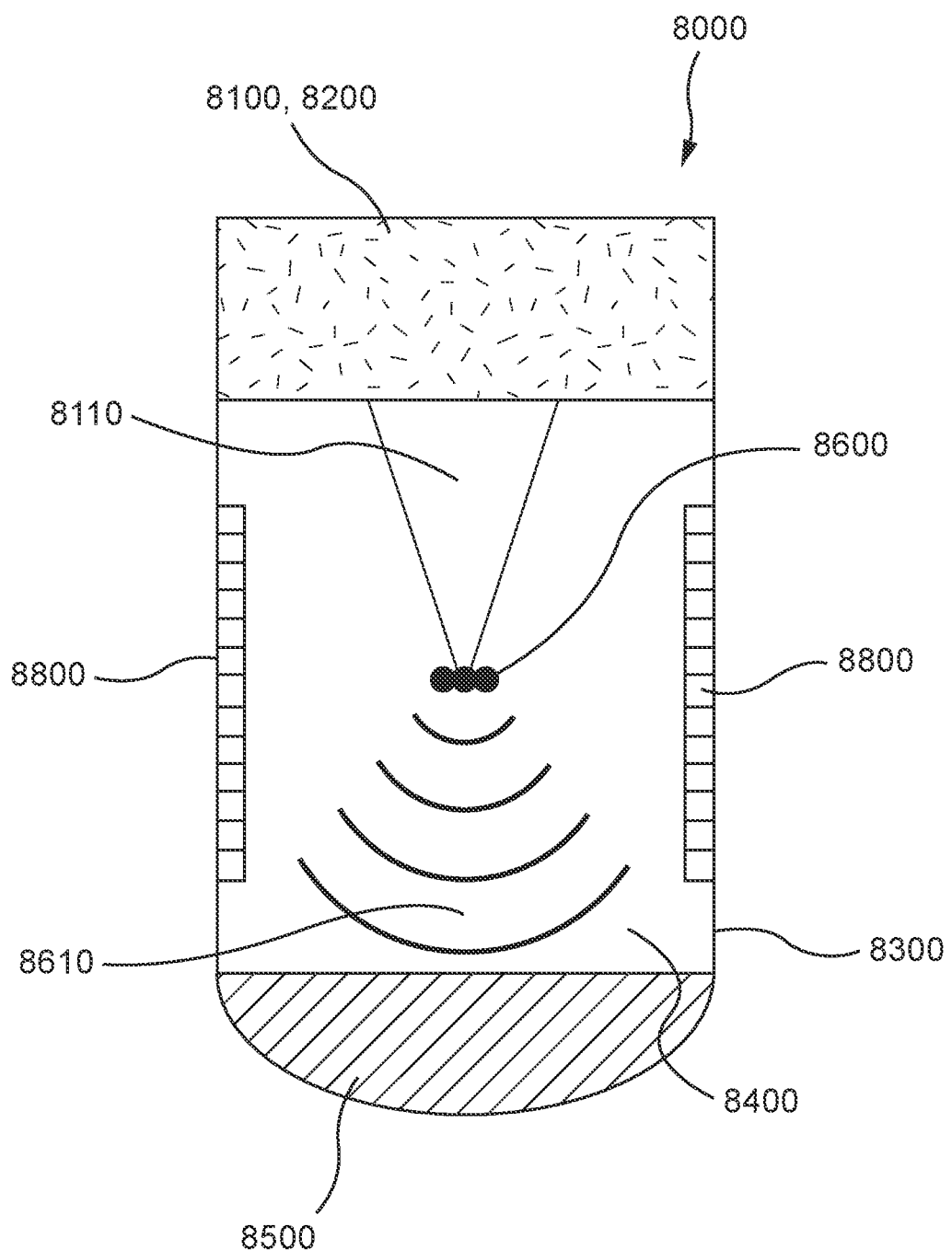
FIG. 8 is an illustration of an exemplary optical breakdown acoustic transducer that includes a plurality of acoustic transmitters to generate a background acoustic field to tune a breakdown process and an acoustic shockwave resulting from the breakdown process.

FIG. 8 shows another exemplary optical breakdown acoustic transducer 8000 where a plurality of acoustic transducers 8800 are used to modify the breakdown process and/or the properties of the acoustic wave 8610. As shown, the optical breakdown acoustic transducer 8000 includes a vessel 8300 that defines a cavity filled with a fluid 8400. A light source 8100 in combination with optical elements 8200 can emit and focus an optical beam 8110, respectively, at a breakdown site 8600 to produce an acoustic wave 8610. An acoustic outlet 8500 disposed at one end of the vessel 8300 can be used to couple the acoustic wave 8610 out into at least a portion of the surrounding medium. The plurality of acoustic transducers 8800 may be disposed along the walls of the cavity of the vessel 8300.

The plurality of acoustic transducers 8800 may emit acoustic waves such that a background pressure field is formed during operation of the optical breakdown acoustic transducer 8800. The background pressure field can generate regions of low and high pressures in the fluid 8400 such that the irradiance threshold and/or the optical-acoustic conversion efficiency is modified. Additionally, once the acoustic shockwave 8610 is generated, the plurality of acoustic transducers 8800 may be used to further modify various aspects of the acoustic shockwave 8610, such as the frequency content, directionality, and amplitude.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An optical breakdown acoustic transducer, comprising:
   a vessel defining a sealed cavity;
   a fluid disposed in the sealed cavity;
   an optical element in optical communication with the fluid and forming at least a portion of a wall of the sealed cavity, the optical element having at least one focal point within the sealed cavity, a first surface in direct contact with the fluid, and a second surface opposite the first surface and not in direct contact with the fluid;
   a pulsed light source, in optical communication with the fluid via the optical element, to emit an optical pulse into the sealed cavity, the optical pulse causing breakdown of the fluid at the at least one focal point, the breakdown of the fluid generating an acoustic shockwave emanating from the at least one focal point; and
   a spatial light modulator (SLM), in optical communication with the pulsed light source, to modify a shape of a wave front of a subsequent optical pulse such that the at least one focal point moves from one or more first positions within the sealed cavity for the optical pulse to one or more second positions for the subsequent optical pulse within the sealed cavity.

2. The optical breakdown acoustic transducer of claim 1, wherein the vessel includes an acoustic outlet to transmit the acoustic shockwave into at least a portion of a medium in contact with the optical breakdown acoustic transducer.

3. The optical breakdown acoustic transducer of claim 2, wherein the acoustic outlet is configured to collimate the acoustic shockwave.

4. The optical breakdown acoustic transducer of claim 2, wherein the acoustic outlet comprises a shape-changeable lens.

5. The optical breakdown acoustic transducer of claim 1, wherein the sealed cavity has dimensions ranging between about 500 nm and about 1000 mm.

6. The optical breakdown acoustic transducer of claim 1, wherein the fluid substantially fills the sealed cavity.

7. The optical breakdown acoustic transducer of claim 1, wherein the pulsed light source emits the optical pulse, the optical pulse having with a pulse duration ranging between about 1 picosecond to about 1 millisecond.

8. The optical breakdown acoustic transducer of claim 1, further comprising: an acoustic modulator, in acoustic communication with the sealed cavity, to tune at least one of a frequency content, directionality, or amplitude of the acoustic shockwave.

9. The optical breakdown acoustic transducer of claim 1, further comprising: an acoustic receiver, in acoustic communication with the sealed cavity, to detect at least a portion of the acoustic shockwave.

10. The optical breakdown acoustic transducer of claim 1, further comprising: at least one acoustic transducer, to modify a pressure distribution within the sealed cavity so as to modify at least one of an irradiance threshold of the fluid or an optical-acoustic conversion efficiency of the breakdown.

11. An optical breakdown acoustic transducer, comprising:
    a pulsed light source to emit a pulsed laser beam;

a beam shaping element, in optical communication with the pulsed light source, to shape a spatial wave front of a first optical pulse of the pulsed laser beam;

a vessel defining a sealed cavity;

a fluid disposed in the sealed cavity;

an optical element, in optical communication with the beam-shaping element and the fluid, to focus the first optical pulse of the pulsed laser beam within the fluid to at least one focal point, the first optical pulse of the pulsed laser beam generating at least one acoustic shockwave by causing breakdown of the fluid at the at least one focal point; and an acoustic outlet, on at least one side of the vessel, to transmit the at least one acoustic shockwave into at least a portion of a medium surrounding the optical breakdown acoustic transducer, wherein the beam shaping element is configured to shape the spatial wave front of a subsequent optical pulse so that the subsequent optical pulse is focused into the sealed cavity to at least one second position that is different from the at least one focal point.

12. The optical breakdown acoustic transducer of claim 11, wherein the beam shaping element is a spatial light modulator.

13. The optical breakdown acoustic transducer of claim 11, wherein the at least one focal point comprises a plurality of focal points and the at least one acoustic shockwave comprises acoustic shockwaves emanating from the plurality of focal points.

14. The optical breakdown acoustic transducer of claim 11, wherein the pulsed laser beam has a peak power of about 1 megawatt to about 1 gigawatt.

15. A method of generating acoustic shockwaves, comprising:

focusing an optical pulse to at least one first position in a fluid disposed in a sealed cavity, thereby generating an acoustic shockwave emanating from the at least one first position due to breakdown of the fluid;

transmitting the acoustic shockwave to a portion of a medium in acoustic communication with the sealed cavity; and changing, with a spatial light modulator, a subsequent wave front of a subsequent optical pulse acted on by the spatial light modulator compared to a wave front of the optical pulse acted on by the spatial light modulator; and focusing the subsequent optical pulse into the sealed cavity to at least one second position that is different from the at least one first position.

16. The method of generating acoustic shockwaves of claim 15, further comprising:

measuring a characteristic of the acoustic shockwave; and focusing a third optical pulse within the fluid so as to generate another acoustic shockwave based on the characteristic of the acoustic shockwave.

17. The method of generating acoustic shockwaves of claim 16, wherein measuring the characteristic comprises measuring at least one of an amplitude, waveform, or spatial radiation pattern of the acoustic shockwave.

18. The method of generating acoustic shockwaves of claim 15, further comprising: measuring an optical property of the breakdown of the fluid.

19. The method of generating acoustic shockwaves of claim 15, further comprising: seeding the at least one position in the fluid prior to breakdown of the fluid to improve effectiveness of generating the acoustic shockwave.

20. The method of generating acoustic shockwaves of claim 15, wherein the portion of the medium includes a sample, and further comprising:

measuring a signal emitted by the sample in response to the acoustic shockwave; and transforming the signal from a time domain representation to a frequency domain representation.

21. The method of generating acoustic shockwaves of claim 20, further comprising: constructing an image of the sample from the signal.

\* \* \* \* \*